United States Patent [19]

Kalopissis et al.

[11] 4,129,644

[45] Dec. 12, 1978

[54] PROTECTING SKIN AND HAIR WITH COSMETIC COMPOSITIONS CONTAINING SUPEROXIDE DISMUTASE

[75] Inventors: Grégoire Kalopissis, Neuilly-sur-Seine; Bernard Jacquet, Antony; Gérard Lang, Deuil-la-Barre, all of France

[73] Assignee: L'Oreal, Paris, France

[21] Appl. No.: 621,629

[22] Filed: Oct. 10, 1975

[30] Foreign Application Priority Data

Oct. 15, 1974 [LU] Luxembourg .................................. 71110

[51] Int. Cl.$^2$ ........................... A61K 7/06; A61K 7/72; A61K 7/48
[52] U.S. Cl. .......................................... 424/59; 8/10.2; 8/11; 195/62; 195/63; 424/70; 424/71; 424/72; 424/94; 424/359; 424/365
[58] Field of Search .................... 424/59, 62, 70, 365, 424/94, 71, 359; 195/62, 63

[56] References Cited

U.S. PATENT DOCUMENTS

| | | | |
|---|---|---|---|
| 3,479,428 | 11/1969 | Bryce et al. | 424/365 X |
| 3,674,902 | 7/1972 | Kalopissis et al. | 424/70 |
| 3,997,402 | 12/1976 | Michelson | 195/62 |

FOREIGN PATENT DOCUMENTS

1171078  11/1969  United Kingdom .................. 424/94

OTHER PUBLICATIONS

Chemical Abstracts, vol. 75, 16390m, (1971).

*Primary Examiner*—Albert T. Meyers
*Assistant Examiner*—Vera C. Clarke
*Attorney, Agent, or Firm*—Cushman, Darby & Cushman

[57] ABSTRACT

A hygienic or cosmetic composition for the hair or skin comprises in a cosmetic vehicle at least one superoxide dismutase.

8 Claims, No Drawings

PROTECTING SKIN AND HAIR WITH COSMETIC COMPOSITIONS CONTAINING SUPEROXIDE DISMUTASE

The present invention relates to the use in cosmetology of certain enzymes and to cosmetic compositions containing these enzymes. More particularly, the present invention relates to the use in cosmetology of superoxide dismutase enzymes and especially to the use of these enzymes in the preparation of hygienic or cosmetic compositions for application to the skin and hair.

It is known that superoxide dismutases are enzymes capable of inducing dismutation of superoxide ions, in accordance with the reaction:

$$2 O_2^- + 2 H^+ \rightarrow H_2O_2 + O_2$$

Superoxide dismutase extracts of ox erythrocytes are disclosed by Markovitz et al. in J. Biol. Chem. 234, p. 40–45, 1959 and superoxide dismutase extracts of *Escherichia coli B* and disclosed by Keele et al. in J. Biol. Chem., 245, p. 6176–6181, 1970.

French patent application Ser. No. 73.13670, filed Apr. 16, 1973, describes superoxide dismutase extracts from marine bacteria strains, as well as a process for their preparation, which process does not form any part of the present invention.

However, this process comprises dispersing a marine bacterial culture in water and maintaining the dispersion at about 4° C. The pH of the medium is then adjusted to 6.5–8, preferably about pH 7, and the temperature of the mixture is then raised to 50°–60° C. for a few minutes. Thereafter the mixture is cooled to about 4° C. and at this temperature the mixture is centrifuged. The resulting supernatant fraction was initially fractionally precipitated by means of neutral salts and the same was again centrifuged. The resulting supernatant fraction was subjected to a second fractional precipitation with neutral salts and again centrifuged. As a variation of this process, a purification step can advantageously be employed. This purification operation comprises dissolving the precipitate resulting from the final fractional precipitation operation in a phosphate buffer at pH 7.8 and dialyzing the resulting solution against the same phosphate buffer at pH 7.8. The enzyme extract of the marine bacterial culture, after dissolving the precipitate from the final centrifugation in the phosphate buffer to pH 7.8 and dialyzing against this same buffer can also be purified by a chromatographic technique using preferably three successive columns which are respectively: a first column of a Sephadex G200 gel, a second column of diethylamino ethyl Sephadex (DEAE-Sephadex A-50) and a third column of a Sephadex G200 gel. To adjust to 6.5–8 the pH of the dispersion of the bacteria in water, that which constitutes the first step of the said process, there is used for example 2N ammonia. Potassium chloride, preferably 3M KCl, is then added thereto.

The mixture thus obtained is then heated to a temperature of 50° to 60° C., for only a few minutes, preferably 3–4 minutes. The mixture is then cooled to about 4° C., the temperature at which all the remaining steps of the process are carried out.

Each of the fractional precipitation operations is carried out, as indicated above, by means of a neutral salt, preferably ammonium sulfate in an aqueous solution.

In an advantageous embodiment of this process, the first fractional precipitation is effected by means of ammonium sulfate added in a quantity such that the concentration of the same in the mixture or treated enzymatic extract is about 30–35 percent of saturation at 4° C. It is noted, however, that all or part of the ammonium sulfate can be replaced by one or more other appropriate salts and the total quantity of said salts is then a quantity equivalent and appropriate so that the same is present in a final concentration of about 30–35% of saturation at 4° C.

As a variant, an ultrafiltration system can be employed which utilizes, for instance, a porous device such as porous tubes, and in particular a system using a first porous retaining tube to concentrate molecules having a molecular weight greater than 40,000 and a second porous tube which passes the molecules of the desired enzyme but retains the remaining bacteria thereby providing a sterile enzymatic extract.

Advantageously the second fractional precipitation can be effected by means of ammonium sulfate, $(NH_4)_2SO_4$, which is added in a quantity such that its concentration in the mixture or treated enzymatic extract is about 70 to 75% of saturation at 4° C.

The superoxide dismutases obtained from different marine bacterial strains by the process described above are all superoxide dismutases which include non-hematinic iron, whereas the enzymes exhibiting an activity of superoxide dismutases which are described in the literature mentioned above, i.e. erythrocuprein and an enzyme extract of *Escherichia coli*, include divalent cations which are, respectively, copper and zinc for the former and manganese for the latter.

The determination of the presence of a metal in the superoxide dismutase can be carried out by a spectrographic analysis of atomic absorption.

This determination can also be effected colorimetrically and consists in coloring an electrophoretic migration gel containing a preparation of the enzyme by means of a specific dye for ferrous iron $Fe^{2+}$, i.e. the bathophenanthroline, optionally in the presence of a reducing agent such as hydrazine. For this test, the gel is divided into two parts lengthwise and one of the two parts is placed in Coomassie Blue (C.I. Acid Blue 92). The other part is placed in the bathophenanthroline. The test is positive if one obtains a pink band in the latter case, on a level of the protein band. As is known, the appearance of such a pink band is considered as an indication of the presence of ferrous iron in the superoxide dismutase protein.

Radioactive iron can also be employed to indicate the protein and to deteremine in it the stoichiometry concerning the divalent metallic cation present therein.

The superoxide-dismutase extracts from marine bacterial cells contain non-hematinic iron, have a molecular weight of 40,000 ± about 2,500, and have an isoelectric point of about 4 to 7. These extracts also exhibit maximum enzymatic activity at a pH of about 8.5 to 10, with an optimum at about pH 9.5.

Their enzyme activity can be maintained over a long period of time by preserving them in a 70–80% solution of neutral ammonium sulfate at 4° C.

The activity of the superoxide dismutase used in the present invention is measured by evaluating its ability to inhibit chemiluminescence reactions caused by an oxygen/hypoxanthine/xanthine oxidase/luminol enzymatic system, as discussed below. This reacting enzymatic system provokes the liberation of $O_2^-$ ions which are capable of producing a chemiluminescence reaction with the luminol. The addition of a superoxide dismutase to this system captures in effect the $O_2^-$ ions and thus causes a reduction of the intensity of the light emitted during this reaction.

The superoxide-dismutase catalyzes in effect the reaction:

$$2 O_2^- + 2 H^+ \rightarrow H_2O_2 + O_2$$

If then there is employed as a substrate in this reaction, the superoxide ions produced by the enzymatic reaction using xanthine oxidase and xanthine or hypoxanthine, the superoxide ions thus produced are very unstable and spontaneously emit light. This latter is, however, much too weak and the measurements are not sufficiently reproducible.

This is why in practice the analytic system is completed by using so as to observe the quantity of superoxide ions formed, a chemiluminescent substance, such as luminol or 5-amino-2,3-dihydro-1,4-phthalazinedione.

$$\text{Luminol} + O_2^- \rightarrow \text{oxidation product} + \text{emission of light}$$

In accordance with a method described in French patent application Ser. No. 73.13670, the activity of superoxide dismutase is measured by using systems producing superoxide ions and catalytic systems susceptible of promoting the oxidation of luminol constituted by $Fe^{2+}$, $Ni^{2+}$ or $Co^{2+}$ ions in aqueous solutions of molecular oxygen in the presence of certain ligands.

The superoxide dismutase introduced in the system reduces the quantity of $O_2^-$ ions and consequently the production of light.

The dosage is effected in the following manner using a reaction mixture consisting of

| Luminol | $10^{-3}$M | 0.3 ml |
|---------|------------|--------|
| Phosphate buffer | $10^{-3}$M, pH 7.8 | 0.3 ml |
| EDTA | $10^{-3}$M | 0.3 ml |
| Water | q.s.p. | 2 ml and |
| 50 μl of xanthine oxidase (1.05 ml of a solution of 1 mg/ml of xanthine oxidase). | | |

This mixture is placed in a silver cell in front of a photomultiplicator. The reaction is initiated by injecting the substrate in the cell with 1 ml of a solution containing 0.3μ mole of hypoxanthine.

There is thus produced an emission of a flux of photons, which creates, under the action of the photomultiplicator, a stream whose intensity is measured and recorded by a picoamperemeter. If there are introduced into the reaction mixture 5 μl of the superoxide dismutase to be evaluated, before the initiation of the reaction, an inhibition of this emission of light is effected.

Thus, arbitrarily, a unit of superoxide dismutase enzyme is defined as being the quantity of this enzyme which causes a 50% inhibition of the emission of light. This unit is then independent on the source of the enzyme and of the superoxide dismutase enzyme used.

The activity of the superoxide dismutase used in the present invention can also be evaluated by causing an inhibition of the same reaction as that mentioned above, directly by injecting 1 ml of a solution of $O_2^-$ ions prepared by electrochemical reduction, (McCord et al., Journal of Biological Chemistry, Vol. 244, 25 (1969) pp. 6049-6055) in 2 ml of a solution containing 0.5μ mole of luminol and 0.17 millimole of phosphate buffer at pH 7.8.

In certain cases, it can be advantageous to estimate over a reasonable period of time the efficacy of the superoxide dismutase in the use considered, by accelerating the oxidation of the materials. This can be accomplished, practically, by using flavines reduced by irradiation at 365 mμ, or by using an enzymatic system such as, for example, a xanthine oxidase/hypoxanthine/oxygen system.

When the oxidation is accelerated by the reduced flavines, a solution of mononucleotide flavine (FMN) $10^{-4}$M in $10^{-3}$M EDTA and $10^{-2}$M phosphate buffer, pH 7.0 is irradiated in a quartz cell placed in a Zeiss spectrofluorimeter, equipped with a M 365 filter; the photoreduction, which is rapidly produced is observed by following the reduction of the intensity of the fluorescence emitted at 530 mμ.

At the end of the reduction, the solution is vigorously agitated in the presence of air, thus resulting in its complete re-oxidation and thereby producing superoxide ions, $O_2^-$. It will be noted that this cycle of reduction-reoxidation of the flavine can be repeated several times, without altering the structure of the mononucleotide flavine. As a variation, the irradiation of a solution as described above at 365 mμ can be effected with uninterrupted agitation by using a B100 A lamp furnished by Ultraviolet Products, Inc.

When it is desired to accelerate the oxidation by the hypoxanthine/xanthine-oxidase/oxygen enzymatic system, it is advantageous to use a solution containing 0.3 ml of $10^{-3}$M hypoxanthine, 0.3 ml of 1 M phosphate buffer (7.8 pH), 0.3 ml of $10^{-3}$ M EDTA, 2.1 ml of water and 0.05 ml of a solution of xanthine oxidase, 1 mg/ml.

It has now been found that superoxide dismutase exhibits properties for the protection of the skin and hair which thus permits its use in cosmetology.

The superoxide-dismutase protects the skin and hair while maintaining the integrity of the natural keratinic structure thereof. It is possible that this protection is due to the inhibition of the oxidation phenomenon of keratin. The superoxide dismutase improves cellular cutaneous respiration and maintains or improves such qualities of the skin as softness to touch, flexibility and elasticity. The presence of superoxide dismutase in compositions for the hair also maintains or improves the condition of the scalp while also protecting the hands of the person applying these compositions thereto.

Further it has been found that the superoxide dismutase protects the skin against inflammations caused by ultra-violet rays. Thus, because of these various characteristics, superoxide dismutase is ideally employed in cosmetic compositions for the skin or hair.

Further, because of their particular oxido-reduction properties, superoxide dismutases are advantageously employed as a protective or stabilization agent for components utilized in cosmetic compositions and especially for those which are susceptible to oxidation or self-oxidation. For example, the superoxide dismutase can prevent or significantly delay fatty bodies present in numerous cosmetic formulations from becoming rancid. More generally, however, the superoxide dismutase inhibits degradation of oxidizable or self-oxidizable components present in cosmetic or hygienic compositions.

It has also been found that superoxide dismutases can inhibit or delay the oxidation of certain strongly oxidizable compounds before their use, such as, for instance:

(a) certain dye compounds or dye precursors used in oxidation dyeing operations where these compounds are developed either by a conventional oxidizing agent such as $H_2O_2$, persulfate, urea peroxide, metallic salts and the like or by the oxygen of the air.

Representative of such dye compounds which are bases, couplers or leuco derivatives are o-aminophenol and derivatives thereof such as those described in French Pat. No. 1,374,983 and its addition French Pat. No. 84,324; 5,6-dihydroxy indole and derivatives thereof, and related amine compounds, for example, those described in French Pat. Nos. 1,133,594; 1,166,712 and 1,264,707; certain leuco derivatives such as those described in French Pat. Nos. 2,056,799 and 2,174,473; and certain bases which are described in French Pat. Nos. 1,473,843; 2,017,995 and 2,016,123;

(b) certain reducing compounds used in compositions for permanently waving hair, for example, alkaline sulfites, mercaptans and derivatives thereof, and principally those disclosed in French Pat. Nos. 1,175,560 and 2,005,648.

In the absence of a superoxide dismutase, the oxidation of a sulfite produces a superoxide anion radical in accordance with the following reaction:

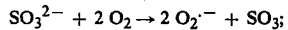

$$SO_3{}^{2-} + 2\,O_2 \rightarrow 2\,O_2{}^{\cdot -} + SO_3;$$

Light irradiation of organic bases, particularly tertiary amines such as triethanolamine used for neutralizing cosmetic compositions containing acid resins (e.g. carboxyvinyl resins such as Carbopol, vinylacetate-crotonic acid resins, or maleic anhydride-containing resins such as Gantrez) favors, in the presence of oxygen, the formation of superoxide ions. By adding a superoxide dismutase, said ions are destroyed, and the oxidation reactions initiated by said ions are prevented.

Titanium oxide or zinc oxide, which are used in numerous cosmetic compositions initiate, when said composition is exposed to light, self-oxidation reactions by formation of superoxide ions.

The present invention thus relates to the use in cosmetology of superoxide dismutase enzymes. This use is principally characterized by the fact that hygienic or cosmetic compositions, for the skin or for the hair, include at least one of said enzymes.

In the present invention, the superoxide dismutases can function as a protective agent for living keratinic substances of the skin and hair. This protective role consists, on the one hand, of maintaining the integrity of the natural keratinic structure of the skin, of the scalp or of the hair, either by preventing or by stopping its degradation and, on the other hand, by maintaining or improving the such qualities of the skin or scalp, as the softness, flexibility and elasticity thereof. This protective role also extends to protecting the skin against harmful effects, notably inflammation reactions, caused by ultra-violet rays.

In accordance with the present invention, the superoxide dismutases can also function as a protective agent for oxidizable or self-oxidizable substances present in cosmetic compositions. Thus the superoxide dismutase can be incorporated into cosmetic or hygienic compositions containing strongly self-oxidizable compounds so as to protect against the oxidation of the said compositions either during storage thereof or during use when said compositions are in contact with keratinic fibers and/or the skin, even if a subsequent oxidation step is utilized.

In particular, there can be mentioned the storage of, or the distribution on hair, of hair coloring compositions (dye compositions and shampoo colorants) formulated with such compounds as p-phenylenediamine and derivatives thereof, o-aminophenols (optionally in the presence of direct dyes) so as to avoid premature self-oxidation which can result in poor penetration of the dye into the fiber. In the latter instance, i.e. where the composition is being used, it is a question of initially temporarily preventing and then retarding this self-oxidation phenomenon.

In a similar manner the use of the superoxide dismutase, in accordance with the invention, provides protection for leuco derivative and dihydroxy indole type compounds before the ultimate development of coloration. These superoxide dismutases also provide protection for sulfhydryl reducing derivatives, during storage or use, which compounds are conventionally employed in compositions used in the first stage of permanent wave operations.

The present invention thus relates to a hygienic or cosmetic composition for the skin or for the hair comprising, in an appropriate excipient, at least one superoxide dismutase enzyme.

The present invention also relates to a cosmetic treatment process comprising applying to the hair or to the skin at least one superoxide dismutase enzyme.

The superoxide dismutase enzymes useful in accordance with the present invention can be of any animal, bacterial or vegetable origin. Representative superoxide dismutases include, without limitation, extracts of bacteria, extracts of mushrooms and extracts of blood.

Representative superoxide dismutase extracts of bacterial origin include, particularly, extracts of *Escherichia coli;* representative superoxide dismutase extracts of mushroom origin include, for instance, extract of *Pleurotus olearius;* representative superoxide dismutase of blood origin includes, in particular, erythrocuprein.

Also usefully employed in the present invention are superoxide dismutase extracts of marine bacterial strains, such as for example, strains of *Photobacterium phosphoreum, Photobacterium leiognathi* or *Photobacterium sepia.* Representative useful strains include the strains of *Photobacterium phosphoreum* No. ATCC 11040, *Photobacterium leiognathi* No. ATCC 25521, *Photobacterium sepia* No. ATCC 15709, *Escherichia coli* No. ATCC 15224 and *Pleurotus olearius Gillet* (Laboratoire de Cryptogamie de Paris).

The superoxide dismutase used in the present invention can be prepared by methods already described in the literature. Thus, superoxide dismutase extracts of marine bacterial strains can be prepared according to the method described in French patent application No. 73.13670 filed Apr. 16, 1973. This process has been described above.

The hygienic or cosmetic composition for application to the skin in accordance with the present invention is principally a solution type lotion; milk type emulsion having a liquid or semi-liquid consistency, obtained by the dispersion of a fatty phase in an aqueous phase, or vice versa; or a cream or gel type suspension or emulsion having a soft consistency.

The compositions of the present invention can be prepared in accordance with conventional procedures and comprise principally cleansing creams, creams for the protection or care of the face, hands or body, for instance day creams, night creams, makeup remover creams, dye foundation creams and anti-solar creams. The compositions of the present invention can also comprise dye foundation fluids, makeup remover milks, milks for the protection or care of the body, anti-solar milks, cleansing lotions, anti-solar lotions, artificial bronzing skin lotions, bath compositions or deodorant compositions containing a bactericidal agent.

The compositions for the skin in accordance with the present invention can also comprise solid preparations such as soaps or cleansing bars. Moreover, these compositions of the present invention which are fluids can be packaged under pressure in an aerosol container together with an aerosol propellant.

The cosmetic or hygienic compositions for the skin in accordance with the present invention can contain, in addition to a superoxide dismutase, active components or excipients which are conventionally employed in such formulations, such as surface active agents, dyes, perfumes, preservatives, emulsifying agents, liquid vehicles such as water, fatty bodies such as natural or synthetic oils destined to constitute the fatty phase of milks or creams, resins of the carboxyvinyl or maleic anhydride type neutralized by tertiary amines and principally by amino alcohols such as triethanolamine. Compounds employed as the fatty phase include for example, sweet almond oil, avocado oil, olive oil, esters of fatty acids such as stearin, glyceryl monostearate or Purcellin oil, ethyl or isopropyl palmitates, alkyl myristates such as propyl, butyl or cetyl myristates. Additionally fatty alcohols such as cetyl alcohol, polyoxyethylenated fatty alcohols or waxes such as for example beeswax or synthetic waxes can also be included in the cosmetic or hygienic composition of this invention.

Compositions for the hair in accordance with the present invention can be provided in the form of aqueous, alcoholic or hydroalcoholic solutions, or in the form of creams, gels, emulsions or even in the form of an aerosol packaged under pressure in an aerosol container together with an aerosol propellant. These compositions for the hair include the superoxide dismutase either as a principal active component or as a protective agent against the oxidation of the other components of said composition.

In addition to conventional active components found in compositions for the hair, the said compositions which can be liquids or gels can also include various conventional adjuvants such as perfumes, dyes, preservatives, sequestering agents, thickening agents and the like.

These compositions for the hair can comprise hair shampoos; hair setting lotions; hair treating lotions; hair styling creams or gels; hair dye compositions, principally oxidation type hair dye compositions, although they can be in the form of a shampoo colorant; hair restructuring lotions; permanent wave compositions and principally compositions employed in the first stage of a permanent waving operation.

Thus, representative compositions for the hair in accordance with the present invention include (a) shampoo compositions containing, in addition to a superoxide dismutase, a cationic, anionic or nonionic detergent; (b) dye compositions, including shampoo colorants, containing dyes or dye precursors such as those already mentioned above, for example m-diamino anisol sulfate, o-, m- or p-aminophenol, nitroparaphenylene diamine, paraphenylene diamine, p-toluene diamine, 5,6-dihydroxy indole and the like; and (c) compositions for the first stage, i.e. reducing stage of a permanent waving operation, containing reducing agents such as mercaptans, sulfites and the like.

The cosmetic compositions in accordance with the present invention can be compositions ready for use as well as concentrates which are diluted before use. The compositions provided in the form of concentrates include, for instance, shampoos or bath compositions. Obviously then the compositions of the present invention are not limited by a particular concentration of the superoxide dismutase contained therein.

Generally, however, the compositions of the present invention which are of the ready to use type include 0.01 to 5 percent by weight, and preferably 0.05 to 1 percent by weight of the superoxide dismutase.

In the case when the oxidizable component to be protected undergoes accelerated decomposition in the presence of keratinic fibers and/or the skin, the superoxide dismutase can be provided alone, in dilute or concentrated aqueous solution or in complex form or as a lyophilizate, and can be added to the other components of the composition at the moment of use.

Also, when the superoxide dismutase is used to maintain or improve the qualities of the skin or hair, they can be added to the composition at the moment of use.

The compositions of the invention can then be provided in the form of a conditioning agent packaged in two or more parts, one part containing the superoxide dismutase and the other part containing the remaining components of the composition. As indicated above, the superoxide dismutase can be provided in the form of an aqueous solution, a complex or a lyophilizate.

The cosmetic treating process of the invention can be effected by employing the hygienic or cosmetic compositions, as defined above, in accordance with procedures conventionally associated with these compositions, such as for example, applying compositions including creams, makeup remover milks or anti-solar compositions to the skin, or applying a hair setting lotion to wet or moist hair or applying, with massaging a shampoo composition to the hair.

The cosmetic treating process of the present invention is carried out so as to apply or deposit a quantity of the superoxide dismutase on the hair or skin in an amount sufficient to obtain the desired protective effect.

Thus the cosmetic treating process is destined either to maintain the keratin structure of the skin or hair, or to maintain or improve such qualities of the skin as softness, flexibility and elasticity, or to protect the skin against the harmful effects of ultra-violet rays.

The following non-limiting examples illustrate the present invention, although Examples 1-3 are included to illustrate processes for preparing superoxide dismutase extracts from bacteria of marine origin, said process being described in French patent application Ser. No. 73.13670.

EXAMPLE 1

*Photobacterium leiognathi* bacteria, strain No. ATCC 25521 is cultivated on a synthetic medium containing, in grams per liter, the following components:

| | |
|---|---|
| NaCl | 30 |
| $Na_2HPO_4 \cdot 12H_2O$ | 18.7 |
| $KH_2PO_4$ | 2 |
| $MgSO_4 \cdot 7H_2O$ | 0.2 |
| $(NH_4)_2HPO_4$ | 0.5 |

-continued

| | |
|---|---|
| Glucose | 1.5 |
| Glycerol | 1.5 |
| Trypticase | 5 |
| Yeast extract | 5 |

The pH of this medium is adjusted to 7.2 with NaOH and the medium is sterilized for 1 hour at 110° C.

One liter of preculture grown overnight and divided into four Erlenmeyer flasks each containing 250 ml of said medium, is employed to inoculate a ferment of 12 liters of medium.

The inoculation of the culture is continued for 12 hours at 20° C. with strong aeration, thus yielding 100 g of bacteria, expressed as moist weight of product.

135 g (moist weight) of *Photobacterium leiognathi* bacteria, resulting from the several cultures are dispersed in 650 ml of water. The resulting dispersion is left to stand at 4° C. overnight. Thereafter, sufficient 2 N ammonia is added to adjust the pH of the medium to 7.5 at which point 18 ml of 3 M KCl are added.

The mixture is then heated to 58° C. and it is maintained at this temperature for 4 minutes. Thereafter the mixture is cooled to 4° C. and centrifuged for 10 minutes at the speed of 10,000 rpm. While continuing to operate at 4° C., the resulting supernatant is adjusted to 35% of saturation with solid ammonium sulfate at pH 8. The supernatant is then centrifuged and the resulting supernatant is adjusted to 75% of saturation by the addition of ammonium sulfate thereto. This mixture is then left to stand overnight at 4° C., after which it is centrifuged, thus yielding precipitated protein which is preserved in a 75% solution of ammonium sulfate.

The activity of a solution of 9 mg of protein per ml (Biuret) was 40 units/mg, whereas the activity of the catalase in a solution of 9 mg of the same protein/mg, as a comparison, was 0 units/mg.

After another fractional precipitation effected with ammonium sulfate at a concentration gradient of 35–75% of saturation, a superoxide dismutase is obtained which, in solution in 14.8 mg of protein/ml (Biuret) exhibits an activity of 134 units/mg to 500 units/mg.

The protein precipitate is dissolved in a phosphate buffer, pH 7.8, and is dialyzed for 48 hours at 4° C. The superoxide dismutase is preserved at $-20°$ C.

To determine the activity of this latter product, a cell containing the following reaction mixture is placed in front of a photomultiplicator:

| | |
|---|---|
| Luminol $10^{-3}$M | 0.3 ml |
| Phosphate buffer $10^{-3}$M, pH 7.8 | 0.3 ml |
| EDTA $10^{-3}$M | 0.3 ml |
| Water | 1.0 ml |
| Xanthine oxidase (1 mg/ml) | 0.050 ml |

The reaction is initiated by injecting into the cell 1 ml of $3 \times 10^{-4}$M hypoxanthine.

A flux of photons was then emitted, which, under the action of the photomultiplicator, produced a stream, the intensity of which was measured with a picoampere meter and recorded.

By introducing into the reaction mixture, before initiation of the reaction, 5μl of a solution of superoxide dismutase prepared as indicated above, the emission of light is inhibited. A unit of superoxide dismutase enzyme is arbitrarily considered to be the quantity of said enzyme which provides a 50% inhibition of emission of light.

Using UV spectroscopy, the superoxide dismutase extract gives a classic spectrum of nonhematinic proteins, with the shoulder of tryptophane at 290 mμ.

To determine the molecular weight, two known techniques are employed, one consisting in determining a centrifugation gradient with sucrose and the other using a Sephadex G200 gel.

The following standards of known molecular weight were employed:

| | M.W. |
|---|---|
| ADH of yeast | 150,000 |
| Bovine albumin | 66,000 |
| Peroxidase | 40,200 |

It was thus determined that molecular weight of the superoxide dismutase was 40,000 ± 2500.

To determine the sub-units of the protein structure of the enzyme, an electrophoresis is carried out employing a polyacrylamide gel to which has been added 10% sodium dodecyl sulfate.

A single type of sub-unit having a molecular weight of about 21,000 is observed. The molecular weight of the superoxide dismutase obtained can then be calculated as 21,000 × 2 or 42,000.

On the polyacrylamide gel, there is obtained a red band in the presence of bathophenanthroline and hydrazine, on precisely the level of the band of superoxide dismutase as revealed by the Coomassie Blue.

A colorimetric dosage of a solution of protein is effected and there is obtained for iron a value which, in estimating the molecular weight of the enzyme at 42,000, gives about 2 atoms of iron per molecule.

A spectrometry of atomic absorption of a solution of protein at 0.2 mg/ml confirms this number.

It is then reasonably estimated that the number of iron atoms per molecule of this superoxide dismutase is 2.

Moreover, the enzyme extract according to this example does not undergo any appreciable or significant loss of activity after 5 minutes at a temperature of 70° C.

An electrofocalization of the superoxide dismutase indicates that the pHi or isoelectric point of this enzyme is 4.4. Further, the enzyme exhibits maximum activity at a pH of about 9.5.

An essentially identical enzyme having similar characteristics is obtained by starting with a bacterial strain of *Photobacterium leiognathi* No. ATCC 25587.

EXAMPLE 2

A culture of *Photobacterium sepia* bacteria, strain No. ATCC 15709, is lysed by agitating in cold water at a rate of 1 g (moist weight) of said bacteria per 4 ml of water. To the light yellow supernatant there is added sufficient 3M KCl to establish a final concentration of 0.1 M.

The resulting solution is heated for 3 to 4 minutes in a water bath at a temperature of 60° C., and then cooled to 4° C. Thereafter the solution is clarified by centrifugation.

The supernatant is fractionally precipitated by the addition thereto of solid ammonium sulfate. The active fraction precipitated between 45 and 75 percent of saturation in ammonium sulfate and the precipitate is separated by centrifugation. The separated precipitate is then redissolved in a minimal volume of $5 \times 10^{-3}$M $K_2HPO_4$, pH 7.8, and is dialyzed overnight against the same phosphate buffer. The product of this dialysis was then put on a column of Sephadex G 100 or G 200 gel, equilibrated with a $5 \times 10^{-3}$M, pH 7.8 phosphate buffer. The active fraction eluted with the aid of a Diaflo PM-10 ultra centrifugation membrane is concentrated and then dialyzed overnight against $5 \times 10^{-3}$M, pH 7.8, $K_2HPO_4$.

The superoxide dismutase enzyme is absorbed on a column of DEAE-Sephadex A-50 buffered with $5 \times 10^{-3}$M $K_2HPO_4$, pH 7.8. The protein is eluted from the column with a linear gradient of $K_2HPO_4$, pH 7.8 (from $5 \times 10^{-3}$M to $3 \times 10^{-1}$M). The superoxide dismutase was thus eluted at a concentration of phosphate of $1.4 \times 10^{-1}$M and then concentrated. Another filtration operation under essentially the same conditions as above was effected on a column of DEAE-Sephadex A-50. The enzyme was eluted at a phosphate concentration of $1.6 \times 10^{-1}$M and concentrated.

The protein thus extracted and purified produces a band singular to electrophoresis on acrylamide gel (100 g of protein per gel).

There are thus obtained 3 mg of pure superoxide dismutase starting with 20 g of gelled cells of *Photobacterium sepia*, with an activity of superoxide dismutase of 250 to 5000 units/mg.

The enzyme activity is maintained over a long period of time by preserving it in a solution of 70-80% $(NH_4)_2SO_4$ at 4° C.

The molecular weight of the purified enzyme is determined by means of ultracentrifugation at 45,000 rpm for 16 hours at 4° C. The speed of sedimentation is measured by the Martin and Ames method, with a linear gradient in sucrose of 5-20 (weight/volume) and by using a Model L2-65B Beckman Spinco machine, with a SW 65K rotor. The sedimentation coefficient was 3.2 for this dismutase, against a coefficient of 4.82 and 7.4 respectively for dehydrogenase alcohols of horse liver and of yeast. Starting with this sedimentation constant, the molecular weight of the superoxide dismutase extract was calculated to be about 42,500. It was also established that the molecule of this protein contains 2 atoms of iron.

Electrophoresis on acrylamide gels indicate for the dismutase a band corresponding to a molecular weight of 20,000 to 20,500, showing thus that the protein molecule was composed of two identical sub units.

The superoxide dismutase was also shown to be very resistant to the proteolytic action of trypsin, since a treatment for 60 minutes of 150 g of this superoxide dismutase with 10µg of trypsin at 20° C. involved no change in the enzymatic activity, nor moreover in the electrophoretic mobility of the non-dissociated protein.

The enzyme obtained was very stable vis-a-vis heat: no loss of enzymatic activity is apparent after 30 minutes at 20° C., 30° C. and even 40° C.; after 15 minutes at 50° C. a 28% reduction of its activity appears; after 30 minutes at 50° C., the loss of activity was always only 50% and it was only from 10% and 50% after, respectively, 3 minutes and 10 minutes at 60° C.

An electrofocalization of the superoxide dismutase indicated an isoelectric point of this enzyme of 4.1.

By means of a solution of $O_2^-$ ions prepared electrolytically, it was determined that the enzyme exhibits maximum activity at a pH of 8.5-10, and an optimum activity at pH 9.5.

EXAMPLE 3

Strain No. ATCC 11040 of *Photobacterium phosphoreum* bacteria which are marine bacteria and have consequently a strong internal saline concentration was treated, as follows.

Lysis of the bacteria was spontaneous in a $10^{-3}$M solution of EDTA, pH 7.8.

The cellular debris was eliminated by means of centrifugation at 16,000 rpm for 20 minutes and at 0° C.

Preliminary studies have shown that the superoxide dismutase enzyme was stable at 50° C. and the other proteins which are thermolabile were eliminated by heating the lysate for 3 minutes at 50° C., after an addition of sufficient KCl to establish a molarity of 0.1. The denatured proteins were separated by conventional centrifugation techniques.

Operating at a temperature of 4° C., the resulting supernatant was fractionally precipitated by the addition of ammonium sulfate in amounts sufficient so that the mixture of treated enzymatic extract has a concentration gradient of about 0 to 30% of saturation at 4° C. The precipitated fraction is removed by centrifuging for 45 minutes at 16,000 rpm at 0° C.

To the resulting supernatant there was added ammonium sulfate in an amount required to establish 75% of saturation at 4° C.

The resulting precipitated fraction was recovered by a centrifugation analogous to the preceding one. To purify the thus extracted superoxide dismutase the recovered precipitate was dissolved in a little phosphate buffer, $5 \times 10^{-3}$M, pH 7.8 and dialyzed against this same buffer for 48 hours at 4° C., to obtain extract A.

The proteins still present were separated as a function of the size of their molecules, with the aid of Sephadex G 100 gel, of which the crosslinking of the particles is such that it excludes the proteins having a molecular weight greater than 100,000, which pass out very rapidly to the exterior of the gel. The molecules whose molecular weight is smaller penetrate the gel and are eluted more or less rapidly according to their size.

To do this, Sephadex resin is put in water and permitted to swell for 3 hours after which the gel is degassed then filtered on a Buchner funnel to eliminate the water. The gel is then placed in the filtration buffer and subsequently poured into a 50 cm long column having a 3 cm internal diameter. The column is equilibrated by passage of 2 liters of buffer therethrough.

The enzymatic extract A produced from the said dialysis is concentrated on a Diaflow millipore membrane (M.W.-10) under nitrogen pressure, up to a volume of 5 ml. This concentrate is then deposited on the column prepared as indicated above and eluted by passage of 500 ml of $5 \times 10^{-3}$M phosphate buffer, pH 7.8 therethrough. The discharge from the column occurred at a rate of a drop every 8 seconds and there was recovered a 2.5 ml fraction, the cells of which, having considerable activity, were collected and concentrated on a Diaflo membrane, thus yielding a concentrated extract B.

A chromatographic purification operation was effected using an ion exchange resin based on DEAE Sephadex. The proteins were eluted according to their charge, by a buffer of increasing ionic strength.

To prepare the column, the resin was put in water and caused to swell. Thereafter the gel was degased and washed in the following two solutions:

(1) 0.5M NaOH and (2) 0.5M $K_2HPO_4$.

The resin was carefully rinsed with distilled water between each step at a pH close to neutral. After filtration on a Buchner the resin was suspended in a 0.1 M phosphate buffer, pH 7.8, and then placed in a 30 cm long column having a 3 cm internal diameter. The column was equilibrated by passing through it 300 ml of 0.1 M buffer.

The concentrated extract B was placed on the column thus prepared and once this extract was completely absorbed, it was eluted with 500 ml of phospate buffer at pH 7.8, composed of 250 ml of 0.1 M phosphate buffer, to which were progressively added 250 ml of 0.5 M phosphate buffer. The discharge was at a rate of a drop every 5 seconds and 2.5 ml of product were recovered. The recovered active fraction was precipitated by ammonium sulfate and then preserved under this form at $-18°$ to $-20°$ C.

The purity of the superoxide dismutase enzyme can be controlled by electrophoresis on a polyacrylamide gel.

The molecular weight of the enzyme was determined from an elution study during its filtration on Sephadex G 200, the relation log (MW) = f (volume of elution) and standards of known molecular weight. The molecular weight thus attributed to the superoxide dismutase extract is about 40,000.

This molecular weight was also determined by a gradient centrifugation of sucrose: sucrose gradients of 5 to 20% were poured into a $5 \times 10^{-3}M$ phosphate buffer, pH 7.8 by progressively mixing 2.60 ml of the 20% solution to 225 ml of the 5% solution, in an appropriate device.

On these sucrose gradients, there were deposited different protein standards of known molecular weight as well as the superoxide dismutase. Equilibrium was effected by centrifugation at 45,000 rpm at 5° C., for 22 hours. The centrifugation tubes were then tapped at the bottom and there were recovered fractions of 10 drops, for which the enzymatic activity exhibited by the different standards used was measured. After having plotted the straight line representing the variation of molecular weights as a function of the number of the fraction of elution, the molecular weight of the superoxide dismutase extract of *Photobacterium phosphoreum* was estimated to be about 40,000, which confirmed the preceding result.

To determine the molecular weight of the sub-units of the protein, the latter, as well as standards of which the molecular weight of sub-units were known were subjected to an electrophoretic migration on polyacrylamide gel in the presence of sodium dodecyl sulfate. The graphic resolution of the values found revealed a value of 20,000 as the molecular weight of each sub-unit of the molecule of the superoxide dismutase which, again, is very stable at 50° C. and exhibits maximum enzymatic activity at a pH of about 9.5.

An electrofocalization of the superoxide dismutase indicates that the pHi or isolectric point of this enzyme is 4.2.

A colorimetric test such as described above confirmed the presence of ferrous iron in the protein, a pink band appearing at the level of the protein band in an electrophoretic migration gel to which previously had been added bathophenanthroline. The number of atoms of ferrous iron per molecule was determined as being practically equal to 2.

EXAMPLE 4 — Study of the photoprotective effect

This test is conducted with the aid of a Xenon, U. V. Solar Simulator device sold by Solar Light Company, Philadelphia, Pa., U.S.A.

The light is produced by an 250 W Xenon arc lamp which has a spectrum similar to that of the sun, the wavelengths range being from 285 nm to 410 nm.

Irradiation with this spectrum reproduces solar erythema. By MED (minimal erythemal dose) time is meant the minimal irradiation which gives erythema 24 or 48 hours after exposure. This quantity is expressed in seconds.

Irradiation is effected on portions of the skin of the backs of voluntary subjects. By controlling the duration of exposure, the MED is first established.

Each subject was then submitted to an irradiation of 5 MED, certain irradiated zones of the skin having previously been treated with the product being studied, mixed with an excipient in a manner to form a cream. Certain irradiated parts of the skin were, prior to irradiation, treated with the excipient alone. Moreover other portions of the skin being irradiated were left untreated.

The product studied was a superoxide dismutase obtained as in Example 1 above.

A subjective evaluation of the intensity of the erythema was made by inspecting the skin 24 or 48 hours after exposure.

Weak erythema is denoted by + and intense erythema by ++. The absence of erythema is designated 0. The results obtained are set forth in the following table:

| Treatment: | skin not treated | skin treated with excipient alone | skin treated with product and excipient |
| --- | --- | --- | --- |
| Subject No. 1 | ++ | + | 0 |
| Subject No. 2 | ++ | ++ | + |
| Subject No. 3 | ++ | ++ | + |

EXAMPLE 5 — Inhibition of the self-oxidation of p-phenylenediamine

A $10^{-3}M$ aqueous solution of p-phenylenediamine in a phosphate buffer, pH 8.6, is prepared. The optical density of the solution, measured at 520 nm at the end of 2 hours, is 0.07. The same solution containing 10 units/ml of the enzyme prepared as in Example 1 above provides an optical density of 0.036 which corresponds to a 49% inhibition.

EXAMPLE 6 — Inhibition of the self-oxidation of 5,6-dihydroxyindole

A $6.7 \times 10^{-5}M$ solution of 5,6-dihydroxy indole in a phosphate buffer, pH 7.8, is prepared. The optical density of the solution, measured at 330 nm increases 0.1 unit/min. In the presence of $407 \times 10^{-9}$ g/ml of the enzyme disclosed in Example 5, the optical density increases only 0.062 unit/min. which corresponds to a 38% inhibition.

EXAMPLE 7 — Inhibition of self-oxidation of 1,2,4-trihydroxy benzene.

A $10^{-3}$ M aqueous solution of 1,2,4-trihydroxy benzene is prepared. 1 ml of this solution is added to 1 ml of phosphate buffer, pH 7.8. The optical density of the resulting solution, measured at 480 nm, increases 0.375 unit/min. On the addition of:

(1) $2 \times 10^{-6}$ g/ml of the enzyme of Example 5, the optical density increases only 0.09 unit/min, which corresponds to a 76% inhibition;

(2) $4 \times 10^{-6}$ g/ml of the same enzyme, the optical density increases only 0.064 unit/min, which corresponds to 83% inhibition; and (3) $40 \times 10^{-6}$ g/ml of the same enzyme, the optical density increases only 0.023 unit/min, which corresponds to a 96.5% inhibition.

EXAMPLE 8 — Inhibition of the self-oxidation of o-aminophenol

A $5 \times 10^{-3}$M aqueous solution of o-aminophenol is prepared. A solution containing the following components is then prepared:
1 ml of bi-distilled water,
1 ml of the above solution and
1 ml of phosphate buffer, pH 9.2.
The optical density of this solution at 430 nm at the end of 15 minutes is 0.22.

On the addition of $2.7 \times 10^{-6}$ g/ml of the enzyme prepared in accordance with Example 1, the optical density at the end of 15 minutes is 0.02 which corresponds to a 91% inhibition. On addition of $27 \times 10^{-6}$ g/ml of the same enzyme the optical density is 0.01 or a 96% inhibition.

EXAMPLE 9 — Inhibition of the self-oxidation initiated by triethanolamine.

Triethanolamine is one of the organic bases currently used for the neutralization of cosmetic compositions containing acid resins, for example carboxyvinyl resins of the Carbopol type.

The tertiary amines of this type form charge transfer complexes with oxygen, and these complexes, under the action of luminous rays, dissociate to give rise to significant quantities of superoxide ions. The latter can cause peroxidations in the cosmetic formulations which contain them. These peroxides, in particular those derived from unsaturated fatty lipids (frequently present in cosmetic compositions for example oleyl alcohol) have a toxic effect and it is desirable to inhibit their formation.

By using as an indicator of the superoxide ion nitrotetrazolium blue (NBT), as described by I. Fridovich et al, Analytical Biochemistry, 44, 276 (1971), it was found that the addition of superoxide dismutase (abbreviated SOD) to an aqueous solution of triethanolamine significantly inhibits the formation of superoxide ions. The SOD used is that obtained in Example 1.

The inhibition of the formation of superoxide ions is evaluated by measuring the optical density at 560 nm and its development as a function of time of irradiation. With a concentration of 0.4% triethanolamine a significant inhibition with SOD concentrations in the order of $10^{-2}$ to $10^{-1}$ mg/cm$^3$ is observed.

Essentially the same results are achieved by replacing the SOD obtained in Example 1 by an essentially equivalent amount of the SOD extract of *Eschierichia coli* or *Pleurotus olearius*.

EXAMPLE 10 — Inhibition of the self-oxidation in the presence of TiO$_2$.

Certain varieties of titanium oxide and zinc oxide lead, on irradiation, to the formation of superoxide ions.

Thus there appears in a suspension of TiO$_2$ in a solution containing nitrotetrazolium blue on irradiation by the sunlight, an intense blue coloration which is indicative of the formation of superoxide ions at the surface of the pigment particles. If the same type of suspension is maintained in the dark, it maintains its initial color.

However, when to the same suspension there is added a solution of superoxide dismutase, there is obtained during irradiation a very distinct inhibition of the blue color.

For this test there is used a suspension of 100 mg of TiO$_2$ in 5 cm$^3$ of a solution of NBT at a concentration of $8 \times 10^{-5}$M. SOD, obtained as in Example 2, is added in amounts of $5 \times 10^{-2}$ mg.

The importance of mineral pigments such as TiO$_2$ and ZnO in cosmetic compositions such as makeup compositions and anti-solar compositions which are exposed during use or storage is well known. The introduction of SOD into these compositions inhibits the formation of superoxide ion and the degradation of the compositions caused thereby.

Essentially the same results can be obtained by replacing the SOD obtained in Example 2 by an essentially equivalent amount of the SOD extract of blood, i.e. erythrocuprein.

EXAMPLE 11 — Inhibition of the self-oxidation of riboflavin.

Cosmetic compositions for the care or treatment of skin often contain riboflavin (vitamin B2). In effect, the presence of this vitamin is necessary to maintain the normal functions of skin.

It is also well kown that when riboflavin is irradiated in the presence of oxygen, superoxide ions are formed which induce peroxidations in the emulsions containing the riboflavin. It is thus desirable and advantageous to add to such riboflavin-containing compositions a superoxide dismutase to inhibit this phenomenon.

EXAMPLE 12 — Foam dye shampoo composition.

The following components are admixed:

| | | |
|---|---|---|
| $C_{12}H_{25}$—O—CH$_2$—CHOH—CH$_2$SO—CH$_2$—CHOH—CH$_2$OH | 10 | g |
| Nonylphenol oxyethylenated with 9 moles of ethylene oxide | 20 | g |
| Copra diethanolamide | 10 | g |
| Butyl glycol | 7 | g |
| Propylene glycol | 15 | g |
| NH$_4$OH, 22° Be, 11 N | 12 | ml |
| Meta-diamino anisole/sulfate | 0.030 | g |
| Resorcin | 0.400 | g |
| M-amino phenol, base | 0.150 | g |
| P-amino phenol, base | 0.087 | g |
| Nitro paraphenylene diamine | 0.004 | g |
| P-toluylene diamine | 1 | g |
| SOD, obtained in Example 3 | 0.05 | g |
| Sodium bisulfite (d = 1.32) | 1.2 | ml |
| Water, q.s.p. | 100 | g |

50 g of this mixture are combined with the same quantity of H$_2$O$_2$ (20 volumes). The resulting product in gel form is then applied to the hair and permitted to remain in contact therewith for 30 minutes. Thereafter the hair is rinsed and dried. On brown hair, there is obtained a chestnut shade. In the above composition, the SOD obtained in Example 3 can be replaced by an essentially equivalent amount of the SOD obtained in Example 1 or Example 2.

EXAMPLE 13 — Hair dye in cream form (oxidation dye).

The following components are admixed to form a cream:

| | | |
|---|---|---|
| Sodium cetyl stearyl sulfate | 3 | g |
| Cetyl stearyl alcohol | 10 | g |
| Oleic diethanolamide | 4 | g |
| Ammonia, 22° Be | 10 | ml |
| M-diamino anisole/sulfate | 0.048 | g |
| Resorcin | 0.420 | g |
| M-aminophenol, base | 0.150 | g |
| Nitro p-phenylenediamine | 0.085 | g |
| P-toluylene diamine | 0.005 | g |
| Sodium bisulfite (d=1.32) | 1.2 | g |
| Superoxide dismutase of Example 1 | 0.1 | g |
| Water, q.s.p. | 100 | g |

30 g of this cream are mixed with 45 g of $H_2O_2$ (20 volumes) and the resulting glossy cream is applied to the hair. After a sufficient contact time therewith, the hair is rinsed and dried.

EXAMPLE 14 — Foam gel or thick solution

The following components are mixed together:

| | | |
|---|---|---|
| Oleyl alcohol oxyethylenated with 12 moles of ethylene oxide | 9 | g |
| Methyl cellulose | 2.5 | g |
| Superoxide dismutase of Example 2 | 0.2 | g |
| Perfume | 0.1 | g |
| Water, q.s.p. | 100 | g |

This composition is applied to the skin. It can also, on the addition of an artifical bronzing agent such as dihydroxyacetone, form a composition for artifically bronzing the skin.

A similar composition is obtained by replacing the SOD of Example 2 by an essentially equivalent amount of the SOD obtained in Example 3.

EXAMPLE 15 — Body cream

| | | |
|---|---|---|
| Cire de Sipol (cetyl stearyl alcohol - partially oxyethylenated) | 5 | g |
| Petrolatum oil | 6 | g |
| Isopropyl myristate | 3 | g |
| Glycerin | 10 | g |
| Perfume | 0.2 | g |
| SOD obtained in Example 3 | 0.5 | g |
| Water, q.s.p. | 100 | g |

A similar cream is obtained by replacing in the above composition the SOD of Example 3 by an essentially equivalent amount of the SOD of Example 1 or the SOD extract of *Pleurotus olearius*.

EXAMPLE 16 — Body cream

| | | |
|---|---|---|
| Cire de Sipol (as in Example 15) | 6 | g |
| Perhydrosqualene | 4 | g |
| Isopropyl palmitate | 2 | g |
| Glycerin | 15 | g |
| Perfume | 0.3 | g |
| SOD of Example 1 | 0.5 | g |
| Water, q.s.p. | 100 | g |

A similar cream is obtained by replacing in the above composition the SOD of Example 1 by an essentially equivalent amount of the SOD extract of *Escherichia coli*, No. ATCC 15224.

EXAMPLE 17 — Beauty milk for the body

| | | |
|---|---|---|
| Purcellin oil | 2 | g |
| Petrolatum oil | 6 | g |
| Oleyl alcohol | 1 | g |
| Isopropyl myristate | 1.5 | g |
| Glycerin monostearate | 2 | g |
| Stearin | 1.4 | g |
| Cetyl alcohol | 0.1 | g |
| Perfume | 0.9 | g |
| Carbopol 941 | 0.35 | g |
| Triethanolamine, pure | 0.35 | g |
| Butyl parahydroxy benzoate | 0.04 | g |
| Preservative agent | 0.3 | g |
| Propylene glycol | 5 | g |
| Rhodorsil antifoam 410 (R.P.) | 0.2 | g |
| Hydroniton - mixture of amino acids, hydrating principles of the skin and sodium allantoin lactate (buffer) | 1.5 | g |
| Ethyl alcohol - 96% | 5 | g |
| Dye - FDC Blue 1 (Kohnstamn) 1% in $H_2O$ | 0.03 | g |
| SOD of Example 1 | 0.08 | g |
| Demineralized water | 71.55 | g |
| | 100.00 | g |

A similar beauty milk is obtained by replacing the SOD obtained in Example 1 by an essentially equivalent amount of the SOD extract of blood (erythrocuprein).

EXAMPLE 18 — Improvement of the condition of in vivo.

The test, made on female rats, involves experimentally modifying the condition of the rats' skin by the action of testosterone propionate, superoxide dismutase having been topically applied to the said skin.

The action of the superoxide dismutase is estimated by clinical examination of the skin and by various biochemical determinations.

1. Experimental record:

Three series of eight female rates, 40 days old, are used.

First series: The rats receive an intra-peritoneal implant of 30–40 mg of testosterone propionate:

Second series: Same treatment as the first series, except that there are applied daily, 5 days per week, 15 units of superoxide dismutase in 0.3 ml of physiologic serum on the previously shaved back of the rats:

Third series: Control, with no treatment. The animals are killed 20 days after the beginning of the test for biochemical determinations.

2. Clinical examination:

The testosterone propionate administered to the female rats of series 1 caused skin modifications which were manifested by an increase in cellular activity at the level of the malpighi layer, an increase in the thickness of the epidermic layer and a significant sebaceous obstruction. The skin became thicker, rougher and less elastic to the touch. The observations were made by three different blind people.

On the other hand, the treated skin of rats in the second series was found to be similar to that of the rats of control series No. 3, i.e. flexible, elastic and soft to the touch.

3. Biochemical determinations:

The following results, obtained on fragments of the treated skin, are reported in the following table and are expressed (1) in milli-units/min and $cm^2$ of skin, and (2) in milli-units/min and mg of protein present in the skin fragments.

Table

Biochemical skin variations as a function of the treatment of female rats, by testosterone propionate combined or not with the topically applied SOD.

|  | Control | Testosterone | Testosterone + SOD |
|---|---|---|---|
| milliunits/min/cm$^2$ | 6600 | 6500 | 10,400 |
| Cytox milliunits/min/mg protein | 13100 | 9500 | 13,700 |

Cytox = cytochrome oxidase

An examination of these results show that superoxide dismutase, administered topically, has a distinct action on the cytochrome oxidases relative to the proteins. Although the testosterone causes a strong reduction, treatment with the SOD provides the same amount as the control rats.

It is known that cytochrome oxidases characterize cellular respiration. The superoxide dismutase improves the skin cellular respiration and such qualities of the skin as softness to touch, flexibility and elasticity.

What is claimed is:

1. A process for maintaining the keratinic structure of the hair comprising applying to the hair an effective amount of at least one superoxide dismutase to maintain the keratinic structure of the hair.

2. The process of claim 1 wherein the superoxide dismutase is an extract of a marine bacterial strain.

3. The process of claim 2 wherein said marine bacterial strain is selected from the group consisting of *Photobacterium phosphorem, Photobacterium leiognathi* and *Photobacterium sepia*.

4. The process of claim 1 wherein said superoxide dismutase is an extract of a member selected from the group consisting of *Photobacterium phosphorem* No. ATCC 11040, *Photobacterium leiognathi* No. ATCC 25521, *Photobacterium sepia*, No. ATCC 15709, *Escherichia coli* No. ATCC 15224 and *Pleurotus Olearius Gillet*.

5. The process of claim 1 wherein said superoxide dismutase is an extract of a member selected from the group consisting of *Escherichia coli, Pleurotus olearius* and *erythrocuprein*.

6. A process for maintaining the keratinic structure of the skin and to maintain or improve the qualities of the skin comprising applying to the skin an effective amount of at least one superoxide dismutase to maintain the keratinic structure of the skin and to maintain or improve the qualities of the skin.

7. A process for protecting the skin from the harmful effects of ultra-violet rays comprising applying to the skin an effective amount of at least one superoxide dismutase to protect the skin from the harmful effects of ultra-violet rays.

8. A process for protecting the skin and hair while maintaining the integrity of the natural keratinic structure thereof comprising applying to said hair or skin a cosmetic composition for the hair or skin comprising a cosmetic vehicle for application to the hair or skin and at least one superoxide dismutase.

* * * * *